United States Patent [19]

Merrill et al.

[11] Patent Number: 5,955,642
[45] Date of Patent: Sep. 21, 1999

[54] GAS PHASE ALKYLATION-LIQUID TRANSALKYLATION PROCESS

[75] Inventors: James T. Merrill, Katy; James R. Butler, Houston, both of Tex.

[73] Assignee: Fina Technology, Inc., Dallas, Tex.

[21] Appl. No.: 08/739,564

[22] Filed: Oct. 30, 1996

[51] Int. Cl.[6] ............... C07C 1/00; C07C 2/64; C07C 2/68; C07C 5/22
[52] U.S. Cl. ............ 585/323; 585/449; 585/450; 585/467; 585/475
[58] Field of Search ................. 585/323, 447, 585/450, 467, 470, 475

[56] References Cited

U.S. PATENT DOCUMENTS

| | | | |
|---|---|---|---|
| 4,107,224 | 8/1978 | Dwyer | 260/671 R |
| 4,169,111 | 9/1979 | Wight | 585/323 |
| 4,185,040 | 1/1980 | Ward et al. | 585/467 |
| 4,284,529 | 8/1981 | Shihabi | 252/455 Z |
| 4,559,314 | 12/1985 | Shihabi | 502/71 |
| 4,772,456 | 9/1988 | DeClippeleir et al. | 423/328 |
| 4,774,377 | 9/1988 | Barger et al. | 585/323 |
| 4,774,379 | 9/1988 | Butler et al. | 585/467 |
| 4,781,906 | 11/1988 | Cahen et al. | 423/328 |
| 4,922,053 | 5/1990 | Wagnespack | 585/449 |
| 4,992,607 | 2/1991 | Harandi et al. | 585/467 |
| 5,030,786 | 7/1991 | Shamshoum et al. | 585/467 |
| 5,157,180 | 10/1992 | West et al. | 585/313 |
| 5,324,877 | 6/1994 | West et al. | 585/467 |

FOREIGN PATENT DOCUMENTS

| | | |
|---|---|---|
| 467007 | 1/1992 | European Pat. Off. . |
| 467007 A1 | 1/1992 | European Pat. Off. . |

OTHER PUBLICATIONS

Kakotailo et al, "Pentasil Family of High Silica Crystalline Materials," Chem. Soc. Special Publ. 33, 133–139 (1980).

Wu et al, "ZSM–5–Type Materials. Factors Affecting Crystal Symmetry," *The Journal of Physical Chemistry*, vol. 83, No. 21, 1979.

Gourgue et al, "Physico–chemical characterization of pentasil type materials, I. Precursors and calcined zeolites," *Zeolites*, 1985, vol. 5, Nov.

Gourgue et al, Physico–chemical characterization of pentasil type materials, II. Thermal analysis of precursors, *Zeolites*, 1985, vol. 5, Nov.

*Primary Examiner*—Walter D. Griffin
*Assistant Examiner*—Thuan D. Dang
*Attorney, Agent, or Firm*—Pamela S. Smith; M. Norwood Cheairs; William D. Jackson

[57] ABSTRACT

An alkylation/transalkylation process involving vapor phase alkylation of a benzene feedstock in a multi-stage alkylation zone having a plurality of series connected catalyst beds containing a pentasil aromatic alkylation catalyst, such as silicalite, coupled with intermediate separation and recirculation steps and liquid phase transalkylation over a transalkylation catalyst comprising a molecular sieve having a pore size greater than the pore size of the silicalite. The benzene containing feedstock is supplied to the multi-stage alkylation reaction zone along with a $C_2$–$C_4$ alkylating agent operated under temperature and pressure conditions to maintain the benzene in the gas phase. Alkylated product is recovered from the alkylation zone and supplied to a benzene recovery zone for the separation of the benzene from the alkylation product. Benzene from the benzene recovery zone is recycled to the reaction zone. A higher boiling bottom fraction containing a mixture of monoalkylated and polyalkylated aromatic components is supplied to a secondary separation zone from which a monoalkylated aromatic component, e.g. ethylbenzene, is recovered overhead with a heavier polyalkylated aromatic recovered as a bottom fraction. The bottom fraction may be applied to a tertiary separation zone.

20 Claims, 5 Drawing Sheets

5,955,642

GAS PHASE ALKYLATION-LIQUID TRANSALKYLATION PROCESS

FIELD OF THE INVENTION

This invention involves an aromatic alkylation/transalkylation process involving vapor phase alkylation of an aromatic substrate such as benzene over a silicalite aromatic alkylation catalyst followed by liquid phase transalkylation over a relatively large pore size zeolite transalkylation catalyst coupled with intermediate separating and recycling steps between a transalkylation reactor and separators.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly- alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

Another example involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The $Na_2O$ content of the zeolite should be less than 0.5 wt. %. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5 and omega crystal types with steam stabilized Y zeolite containing about 0.2% $Na_2O$ being preferred. The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-β, zeolite-Y or zeolite-Ω or in the vapor phase employing a catalyst such as silicalite or ZSM-5. In the Butler process where vapor phase alkylation is followed by liquid phase transalkylation, substantial quantities of water may be included in the feedstream to the alkylation reactor. In this case, the feed to the transalkylation reactor may be dehydrated to lower the water content. The transalkylation catalyst may take the form of a zeolite-Y or zeolite-Ω.

SUMMARY OF THE INVENTION

In accordance with the present invention, there is provided an alkylation/transalkylation process involving vapor phase alkylation of a benzene feedstock in a multi-stage alkylation zone having a plurality of series connected catalyst beds containing a pentasil aromatic alkylation catalyst, preferably silicalite, coupled with intermediate separation and recirculation steps and liquid phase transalkylation over a transalkylation catalyst comprising a molecular sieve having a pore size greater than the pore size of the silicalite. In one embodiment of the invention, a benzene containing feedstock is supplied to the multi-stage alkylation reaction zone along with a $C_2$–$C_4$ alkylating agent. The multi-stage alkylation zone is operated under temperature and pressure conditions to maintain the benzene in the gas phase. Alkylated product is recovered from the alkylation zone and supplied to a benzene recovery zone for the separation of the benzene substrate from the alkylation product. Benzene is recovered from the benzene recovery zone and recycled to the reaction zone. Higher boiling bottom fraction containing a mixture of monoalkylated and polyalkylated aromatic components is supplied to a secondary separation zone from which a monoalkylated aromatic component, e.g. ethylbenzene, is recovered overhead. A heavier polyalkylated aromatic is recovered as a bottom fraction. In one embodiment of the present invention, this bottom fraction is applied to a tertiary separation zone as described below. In another embodiment of the invention, the bottom fraction from the secondary separation zone is divided into a first portion which includes dialkylated and trialkylated aromatics and which is supplied to a transalkylation zone containing a molecular sieve catalyst as described above. A second portion of the polyalkylated component recovered from the secondary separation zone is supplied to a tertiary separation zone which is operated to separate this stream into a lower boiling fraction comprising dialkyl and trialkyl aromatics and a higher boiling fraction comprises a residue which can be disposed of. The lower boiling fraction from the tertiary separation zone is supplied to the transalkylation reaction zone together with the first portion of the second separation zone. Benzene is also supplied to the transalkylation reactor which is operated under temperature and pressure conditions to maintain the benzene in the liquid phase to cause disproportion of the polyalkylated aromatic fraction to produce a transalkylated product having a reduced polyalkylbenzene content and an enhanced monoalkylbenzene content. At least a portion of the transalkylated product is supplied to the benzene recovery zone. Preferably, the product output from the secondary separation zone is divided such that the weight ratio of the first portion, supplied directly to the transalkylation reactor to the second portion which is first supplied to the tertiary separation zone is within the range of 1:3 to 3:1 and more preferably within the range, 1:2 to 2:1.

In yet a further aspect of the invention, the benzene recovery zone is operated in two stages. A first prefractionating stage and a second stage in which benzene is recovered overhead with benzene and mono- and poly- alkylated aromatics recovered as a bottoms fraction and a second stage from which an additional benzene is recovered overhead and recycled along with that from the first stage to the benzene reaction zone. In this embodiment of the invention, at least a portion of the disproportionation product from the transalkylation reactor is supplied to the first stage of the benzene recovery zone, preferably substantially all of this disproportionation is supplied to the first stage.

A preferred alkylation catalyst for use in the present invention is silicalite having a relatively small crystal size and formulated with an alumina binder to provide catalyst particles having a high surface area, preferably having a surface/volume ratio of at least 60 in.$^{-1}$ Preferably this silicalite, which is predominately monoclinic silicalite, has a crystal size of about 0.5$\mu$ or less.

In yet a further embodiment of the invention, the alkylation reaction zone has at least three and preferably at least four series connected catalyst stages, each containing a silicalite aromatic alkylation catalyst. The alkylating agent introduced to the alkylation reaction one along with the aromatic substrate is supplied in a manner to provide for the introduction of an initial portion of the alkylating agent together with benzene to the top of the first catalyst bed with the additional interstage injection of a second portion of the alkylating agent between at least some of the catalyst beds. This is accomplished without the accompanying interstage injection of benzene in a mole excess of the alkylating agent. Stated otherwise, in contrast to the conventional practice of injecting substantial quantities of benzene between catalyst beds, benzene interstage injection is reduced, if not eliminated entirely. Preferably, the reaction zone is operated to provide an average temperature for the reaction zone of no more than 800° F.

DETAILED DESCRIPTION OF THE INVENTION

Figure 1:
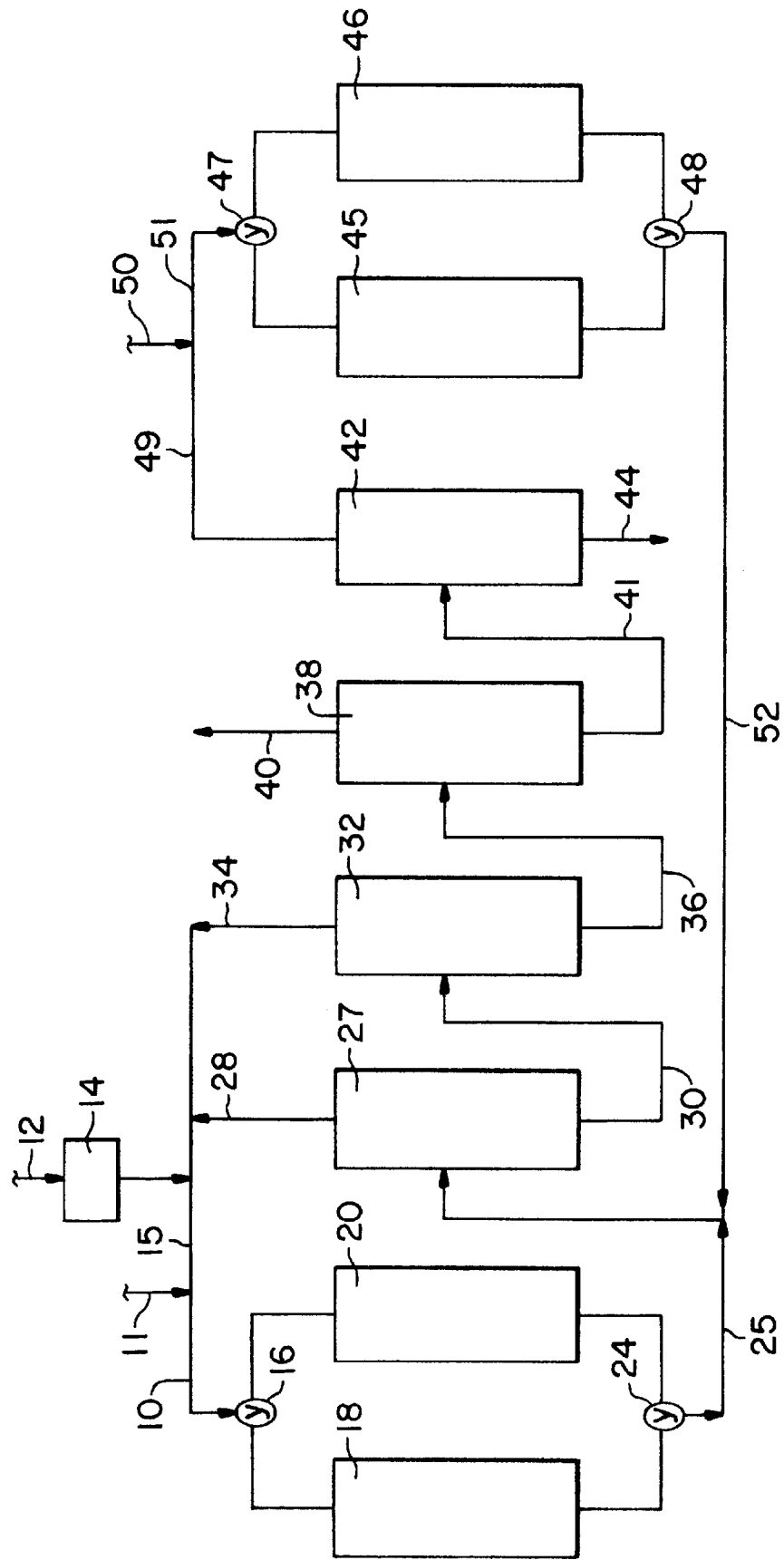
FIG. 1 is a simplified schematic flow diagram illustrating one embodiment of the invention in which the output from a transalkylation reactor is recycled to the initial stage of a two stage benzene separation zone.

The present invention involves vapor phase alkylation of an aromatic substrate comprising benzene in a multistage reaction zone followed by liquid phase transalkylation in which the alkylation and transalkylation reactors are integrated with intermediate separation zones in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The alkylation reactor is a multistage reaction zone containing at least three series connected catalyst beds which contain a pentasil molecular sieve aromatic alkylation catalyst, preferably a silicalite alkylation catalyst. As described in greater detail below the silicalite alkylation catalyst, preferably is silicalite characterized as having a high monoclinicity and a small sodium content. The preferred catalyst used in the transalkylation reactor is zeolite Y.

As will be described in greater detail below, the alkylation reactor is operated at substantially higher temperature conditions than the transalkylation reactor and in one embodiment of the invention, the recycled output from the transalkylation reactor is passed in a heat exchange relationship with the alkylation reactor product feed to the initial benzene separation zone.

A preferred embodiment of the invention involves a multistage alkylation reactor with the output coupled to a four-stage separation system which in turn supplies a polyethylbenzene feed to a transalkylation reactor. In the embodiment of the invention described herein, parallel alkylation and transalkylation reactors are employed so that simultaneous catalyst regeneration can occur during operation of the alkylation and transalkylation reactions. Preferably the alkylation reactor comprises at least four catalyst beds. More beds can be provided, and it will sometimes be advantageous to provide at least five catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone of the type involved in the present invention, benzene and ethylene (or other alkylating agent) is introduced as a mixture to the first catalyst bed at the top of the reaction zone and also in between the several successive stages of catalyst beds. In the present invention, ethylene is supplied along with benzene to the top of the catalyst bed top of the reactor. In addition, interstage injection of ethylene and benzene is provided for between the subsequent catalyst beds. The benzene to ethylene mole ratio is about 18 as injected into the top of the alkylation reactor and progressively decreases because of the interstage injection of ethylene and of course the alkylation of the benzene to ethyl benzene and polyethylbenzenes.

The silicalite alkylation catalyst employed in the present invention does not require the presence of water to stabilize the catalyst, so a water or steam co-feed, as is sometimes used in connection with silicalite, is not called for in this invention. Interstage injection of ethylene is normally employed. The interstage injection of the benzene or other aromatic substrate can also be provided for. The mole ratio of the aromatic substrate to the ethylene at the interstage injection points can vary from zero (no benzene injection) up to about five. The benzene in many cases will be employed in an amount less than the amount of ethylene on a mole basis. Stated otherwise, benzene can either not be injected between the catalyst beds or, if injected, can be employed in a relatively minor amount, i.e., a mole ratio of benzene to ethylene of less than one. On the other hand, the mole ratio of the aromatic substrate to the alkylating agent can be as high as five. This is coupled with a somewhat lower operating temperature than would normally be the case for vapor phase alkylation. In the preferred embodiment of the invention, the temperature of the benzene stream into the top of the alkylation reactor will be in the order of 720° F. or lower. The alkylation reaction is, of course, an exothermic reaction so that the temperature will be increased progressively throughout the alkylation column as noted previously.

The alkylation catalyst employed in the present invention is a molecular sieve from the pentasil family of high silica molecular sieves or zeolites. Such pentasil molecular sieves are described, for example, in Kokotailo et al, "Pentasil Family of High Silica Crystalline Materials," Chem. Soc. Special Publ. 33, 133–139 (1980). These molecular sieves pentasils can include high silica alumina ratio ZSM-5, such as described, for example, in Wu et al, "ZSM-5-Type Materials. Factors Affecting Crystal Symmetry," *The Journal of Physical Chemistry*, Vol. 83, No. 21, 1979, or silicalite molecular sieves, as described, for example, in Gourgue et al, "Physico-chemical characterization of pentasil type materials, I. Precursors and calcined zeolites," *Zeolites*, 1985, Vol. 5, November, and Gourgue et al, "Physico-chemical characterization of pentasil type materials, II. Thermal analysis of the precursors, *Zeolites*, 1985, Vol 5, November.

The silicalite or other pentasil molecular sieve alkylation catalyst has a somewhat smaller pore size than the preferred zeolite-Y employed in the transalkylation reactor. The preferred silicalite catalyst has a somewhat smaller crystal size than is usually the case. Preferably, the crystal size is about 0.5μ, or even somewhat smaller, as contrasted with a crystal sizes of perhaps 1–2μ for similar catalysts.

A preferred silicalite for use in the present invention is extruded with an alumina binder in a "trilobe" shape having a nominal diameter of about 1/16" and a length of the extrudate of about 1/8–1/4". The "trilobe" cross sectional shape is something on the order of a three leaf clover. The purpose of this shape is to increase the surface area of the extruded catalyst beyond what one would expect with a normal cylindrical extrudate. The preferred silicalite catalyst is characterized as monoclinic silicalite. Monoclinic silicalite may be prepared as disclosed in U.S. Pat. Nos. 4,781,906 to Cahen et al and 4,772,456 to DeClippeleir et al. Preferably the catalysts will have near 100% monoclinicity) although silicalite catalysts that are 70–80% monoclinic and about 20–30% orthorhombic symmetry may be used in the preferred embodiment of the invention. The silicalite preferably is present in an amount of 75–80 wt. % with the alumina binder being present in an amount of 20–25 wt. %. The silica/alumina ratio of the preferred silicalite is about 200, or more normally, 225. The silicalite may have an alpha value of about 20–30. The "alpha value" is characterized in terms of the activity of a catalyst for tracking hexane as disclosed in U.S. Pat. Nos. 4,284,529 to Shihabi and 4,559,314 to Shihabi. The catalyst contains small amounts of sodium and iron.

The preferred silicalite catalyst has a crystal structure characterized by an aluminum rich outer shell and an aluminum deficient interior portion when compared with the outer shell. The silicalite catalyst is dry and has no appreciable or intended water content. The alumni binder is a high purity alumina such as "catapal alumina." The silicalite catalyst preferably contains only a small amount of sodium, about 70–200 ppm sodium oxide, and contains only a small amount of iron oxide, about 300–600 ppm. The catalyst need not contain any additional "promoter" metals incorporated during the synthesis of the catalyst.

Referring now to FIG. 1, an input feed stream is supplied by fresh ethylene through line 11 and fresh benzene through line 12. The feedstream is applied through a two position valve 16 and inlet line 17 to the top of an alkylation reaction zone 18 which comprises a plurality of series connected catalyst beds each of which contains a silicalite alkylation catalyst. The reactor is operated at an average temperature, preferably within the range of 700° F.–800° F. and at pressure conditions of about 200 to 350 psia, to maintain the benzene in the gaseous phase.

Figure 2:
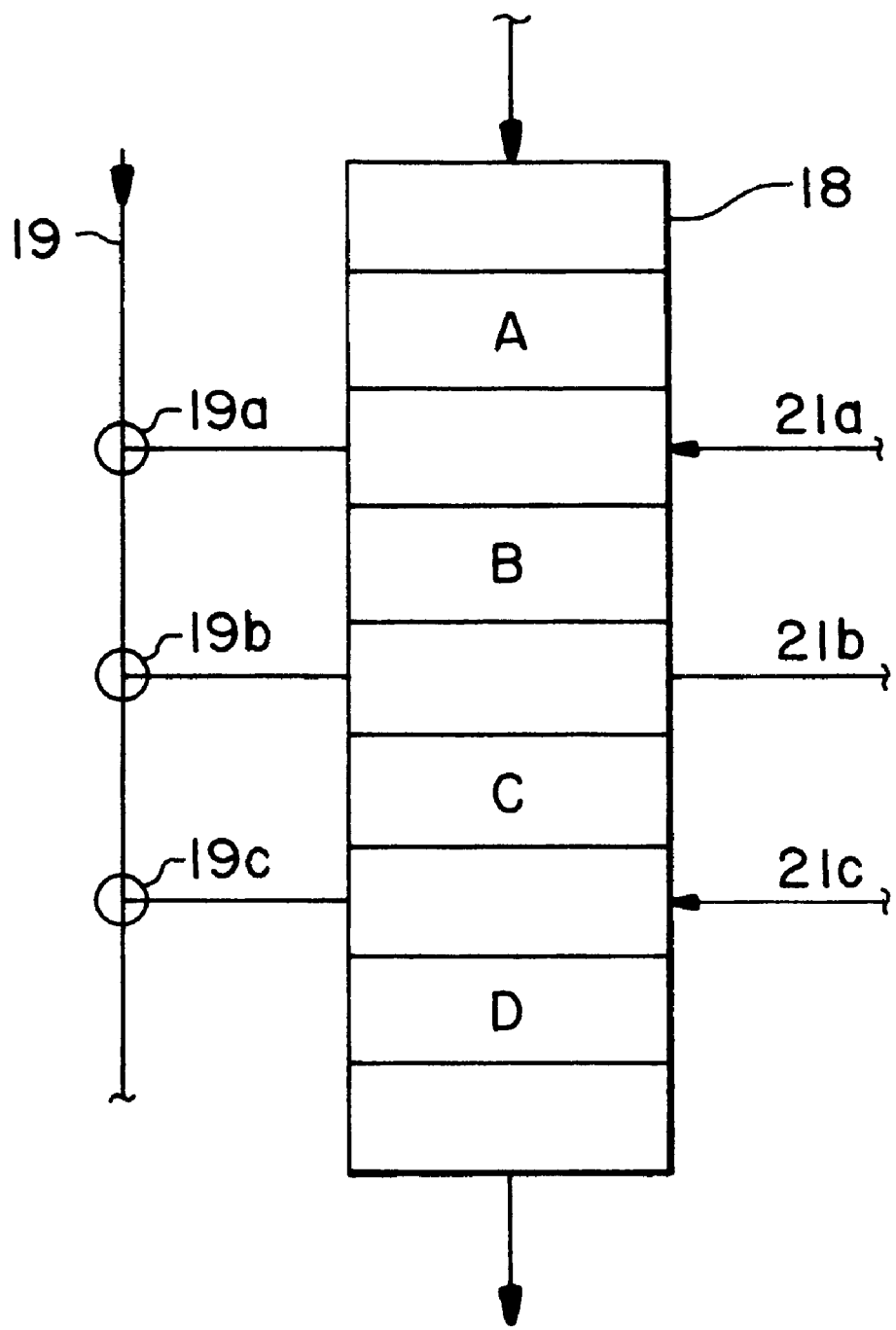
FIG. 2 is a schematic illustration of an alkylation reaction zone comprising four series connected catalyst beds showing the introduction of benzene and ethylene, or other alkylating agent, to the initial catalyst beds with subsequent interstage injection of ethylene.

A second reaction zone 20 is schematically shown to be in the "off-line" position for regeneration of the catalyst. In an alternative mode of operation, both reaction zones 18 and 20 are operated in a parallel mode of operation in which they are both in service at the same time. That is, valve 16 is configured so that all of the flow from line 10 is directed to the top of reactor 18. As shown in detail in FIG. 2, the reactor 18 comprises four series connected catalyst beds designated as beds A, B, C and D. An ethylene feed stream is supplied via line 19 and proportionating valves 19a, 19b and 19c to provide for the appropriate interstage injection of ethylene. Benzene can also be introduced between the catalyst stages by means of secondary benzene supply lines 21a, 21b and 22b, respectively. As will be recognized, the parallel reactor 20 will be configured with similar manifolding as shown in FIG. 2 with respect to reactor 18.

Returning to FIG. 1, the effluent stream from the alkylation reactor 18 is supplied through a two position outlet valve 24 and outlet line 25 to a two-stage benzene recovery zone which comprises as the first stage a prefractionation column 27. Column 27 is operated to provide a light overhead fraction including benzene which is supplied via line 28 to line 15 where it is mixed with benzene from line 12 and then to the alkylation reactor input line 10. A heavier liquid fraction containing benzene, ethylbenzene and polyethylbenzene is supplied via line 30 to the second stage 32 of the benzene separation zone. Stages 27 and 32 may take the form of distillation columns of any suitable type, typically, columns having from about 20–60 trays. The overheads fraction from column 32 contains the remaining benzene which is recycled via line 34 to the alkylation reactor input. The heavier bottoms fraction from column 32 is supplied via line 36 to a secondary separation zone 38 for the recovery of monoalkylated aromatic component, e.g. ethylbenzene. The overheads fraction from column 38 comprises relatively pure ethylbenzene which is supplied to storage or to any suitable product destination by way of line 40. By way of example, the ethylbenzene may be used as a feedstream to a styrene plant in which styrene is produced by the dehydrogenation of ethylbenzene. The bottoms fraction containing polyethylbenzenes, heavier aromatics and normally only a small amount of ethylbenzene is supplied through line 41 to a tertiary polyethylbenzene separation zone 42. The bottoms fraction of column 42 comprises a residue which can be withdrawn from the process via line 44 for further use in any suitable manner. The overhead fraction from column 42 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 45 and 46 are provided through inlet and outlet connections involving valves 47 and 48. While one transalkylation reactor is on-stream, the other can be undergoing regeneration operation in order to bum coke off the catalyst beds. Alternatively, both of reactors 45 and 46 can be placed on stream at the same time so that both are in service in a parallel mode of operation. By minimizing the amount of ethylbenzene recovered from the bottom of column 38, the ethylbenzene content of the transalkylation feedstream can be kept small in order to drive the transalkylation reaction in the direction of ethylbenzene production. The polyethylbenzene fraction withdrawn overhead from column 42 through line 49 is mixed with benzene supplied via line 50 and then supplied to the on-line transalkylation reactor 45 via line 51. Preferably, the benzene feed supplied via line 50 is of relatively low water content, about 0.05 wt. % or less. Preferably, the water content is reduced to a level of about 0.02 wt. % or less and more preferably to no more than 0.01 wt. %. The transalkylation reactor is operated as described before in order to maintain the benzene and alkylated benzenes within the transalkylation reactor in the liquid phase. Typically, the alkylation reactor and transalkylation reactor may be operated to provide an average temperature within the transalkylation reactor of about 150° F.–550° F. and an average pressure of about 600 psi. The preferred catalyst employed in the transalkylation reactor is zeolite Y having the characteristics described previously. The weight ratio of benzene to polyethylbenzene should be at least 1:1 and preferably is within the range of 1:1 to 4:1.

The output from the transalkylation reactor containing benzene, ethylbenzene and diminished amounts of polyethylbenzene is supplied via line 52 to the initial stage of the benzene recovery zone. This mode of operation is contrary to the normal mode of operation as disclosed in the aforementioned EPA 467,007 to Butler. As disclosed there, the output from the transalkylation reactor is supplied to the second stage of the benzene recovery zone, corresponding to column 32 in FIG. 1. While this mode of operation can be followed in carrying out the present invention, it is preferred to operate, as shown in FIG. 1, in which the transalkylation reactor output is supplied to the initial stage 27 of the benzene recovery zone. This offers the advantage of having a stream with approximately the same benzene and ethylbenzene composition as the stream from the alkylation reaction.

In the process shown schematically in FIG. 1, the entire bottoms fraction from the ethylbenzene separation column 38 is applied to the tertiary separation column 42 with overhead fractions from this zone then applied to the transalkylation reactor. This mode of operation offers the advantage of relatively long cycle lengths of the catalyst in the transalkylation reactor between regeneration of the catalyst to increase the catalyst activity. Another embodiment of the invention achieves this advantage by supplying a portion of the output from the ethylbenzene separation column directly to the transalkylation reactor. Surprisingly, by employing vapor phase alkylation coupled with liquid phase transalkylation in accordance with the present invention, a significant quantity of the bottoms fraction from the ethylbenzene column can be sent directly to the transalkylation reactors thus decreasing the amount of residue which is lost from the process. While applicants' invention is not to be limited by theory, it is believed that direct application of a substantial portion of the output from the ethylbenzene separation zone to the transalkylation reactor is made possible, at least in part, by the low water content in the process stream resulting from low water content introduced initially into the transalkylation reactor.

Figure 3:
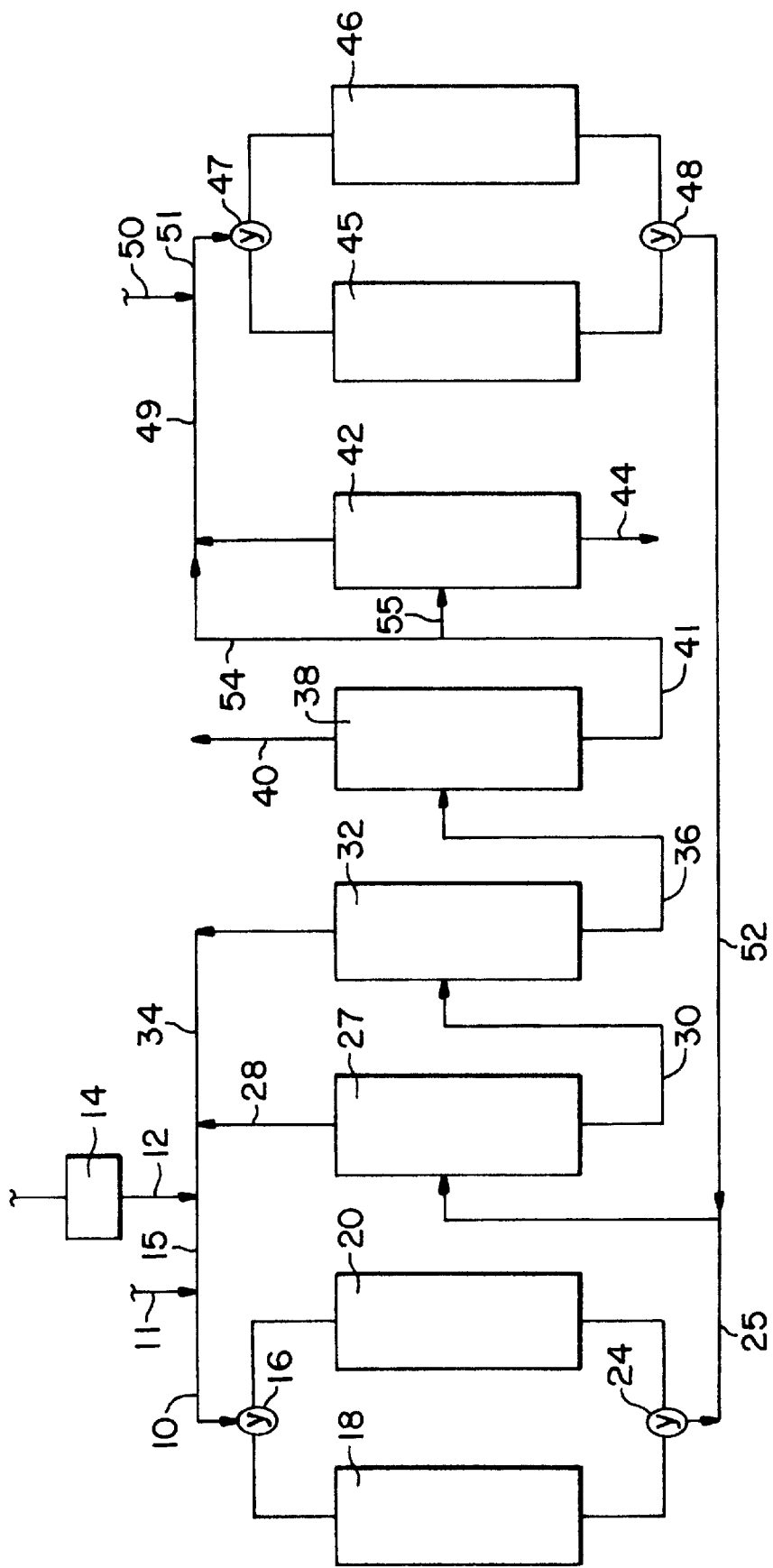
FIG. 3 is a schematic illustration of a preferred embodiment of the invention in which the bottoms fraction of an ethylbenzene recovery separation zone is separated with a first portion thereof being supplied directly to a transalkylation reaction zone and second portion being supplied to a trialkyl benzene column with separation of a residue fraction and cycling of the overhead fraction to the transalkylation reaction zone.

This embodiment of the invention is shown in FIG. 3 in which like elements and components as are shown in FIG. 1 are illustrated by the same reference numerals as used in FIG. 1. As shown in FIG. 3, a portion of the bottoms fraction from the secondary separation zone 38 is supplied directly to the transalkylation reactor 45 via line 54. A second portion of the bottoms fraction from the ethylbenzene column is applied to the tertiary separation column 42 via line 55. The overhead fraction from column 42 is commingled with the bypass effluent in line 54 and the resulting mixture is fed to the transalkylation reactor via line 47. By bypassing the column 42 with a substantial portion of the bottoms product from column 38, the residue which is lost from the system can be reduced. In a preferred embodiment of the invention, a substantial amount of the bottoms product from column 38 is sent directly to the transalkylation reactor, bypassing the polyethylbenzene column 42. Normally, the weight ratio of the first portion supplied via line 54 directly to the transalkylation reactor to the second portion supplied initially via line 55 to the polyethylbenzene would be within the range of about 1:2 to about 2:1. However, the relative amounts may vary somewhat more widely to be within the range of a weight ratio of the first portion to the second portion in a ratio of about 1:3 to 3:1.

In a further aspect of the present invention, the embodiment of either FIG. 1 or FIG. 3 may be coupled with a novel heat integration and heat exchange procedure in order to improve the thermal energy relationships encountered in carrying out the alkylation/transalkylation process of the present invention. Various feedstreams and recycle streams involved in the present invention are incorporated into the integrated heat exchange process as described in co-pending Application Ser. No. 08/739,897 filed of even date herewith by James Merrill et al, entitled "Heat Integration in Alkylation/Transalkylation Process" and further identified by attorney docket number FINT B8153. The incorporation of this concept of heat integration in the processes of the present invention is illustrated in FIGS. 4 and 5.

Figure 4:
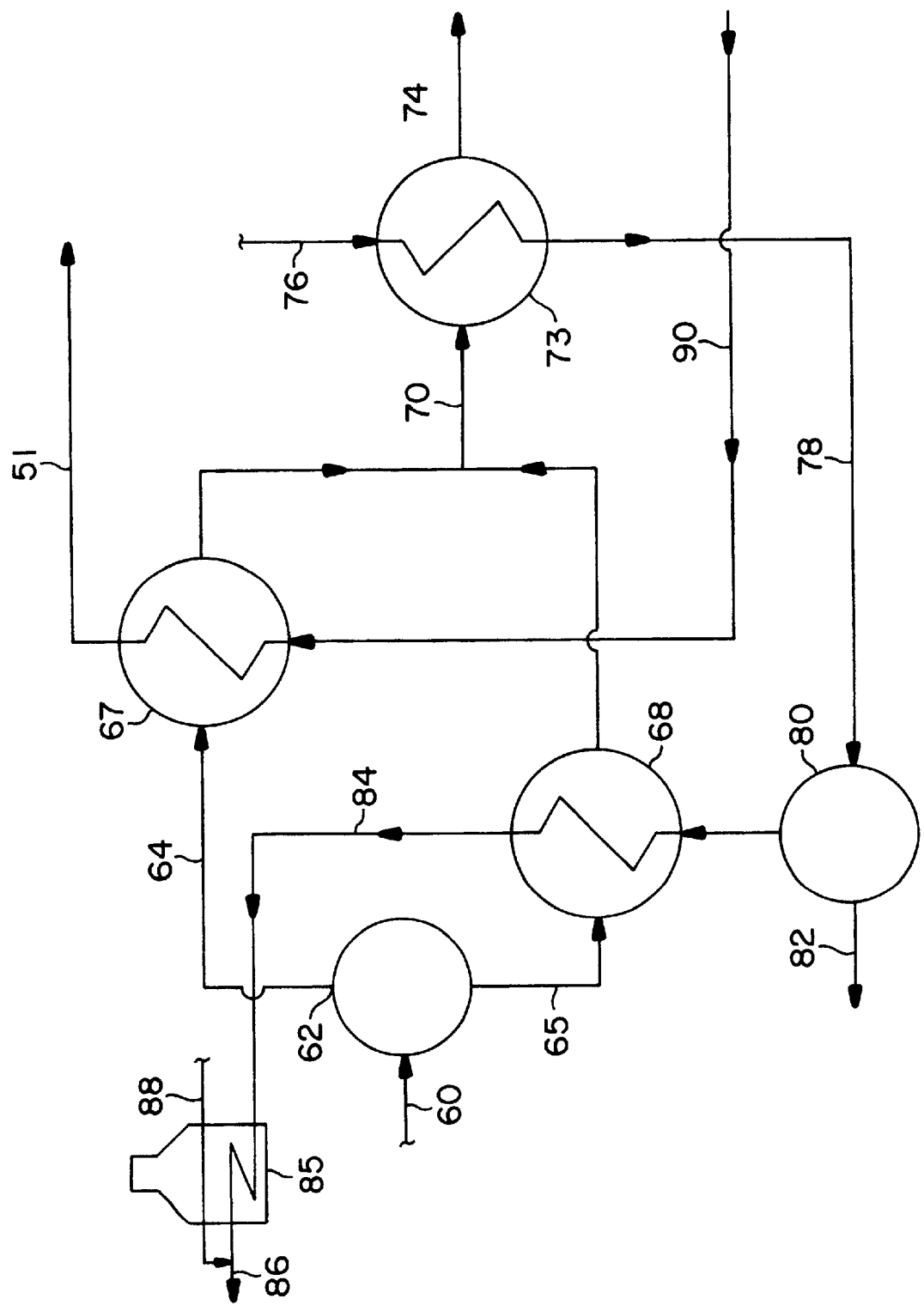
FIG. 4 is a schematic illustration showing preferred form of the process scheme of FIG. 1 employing a preferred arrangement of heat exchangers in the flow scheme between the alkylation reaction zone and the benzene separation zone.

Turning first to FIG. 4, there is illustrated a line 60, corresponding generally to line 25 as shown in FIGS. 1 and 3, from which effluent from the alkylation reactor (not shown in FIG. 4) is passed to a splitter 62 where it is divided into streams 64 and 65 and passed through heat exchangers 67 and 68, respectively. The flow streams from heat exchangers 67 and 68 are combined into stream 70 and then passed through a third heat exchanger 73 into a line 74 leading to the initial benzene separation zone 27 (shown in FIGS. 1 and 3). In the third heat exchanger 73, recycled benzene withdrawn from benzene column 27 and column 32, and fresh benzene supplied via line 12 (FIGS. 1 and 3) is passed via line 76, corresponding generally to line 15 in FIGS. 1 and 3, in indirect heat exchange with the alkylation reactor output and then withdrawn via line 78 and passed to a proportionating valve 80. The proportionating valve 80 may be adjusted to direct the flow stream in line 78 entirely through the first heat exchanger 68 where it is ultimately directed to the top of the alkylation reactor 18, or a portion may be applied through line 82 to provide for the interstage injection of benzene in accordance with the protocol discussed previously with reference to FIG. 2. The output from heat exchanger 68 is supplied via line 84 to a heater 85 where the benzene stream is heated as necessary, e.g. to 700° F., and then applied through a line 86 to the initial bed of the alkylation reactor. A second recycle stream from the benzene recycle stream 15 (FIGS. 1 and 3) is applied through line 88 to heater 85 and then fed to line 86 for introduction into the top of the alkylation reactor. The feedstream to the top of the transalkylation reactor is supplied via line 90 (corresponding to line 51 of FIGS. 1 and 3) to heat exchanger 67 in indirect heat exchange with the split portion of the alkylation reactor effluent and then through valve 47 (FIGS. 1 and 3) to the appropriate on-stream transalkylation reactor or to both reactors in a parallel mode of operation.

Figure 5:
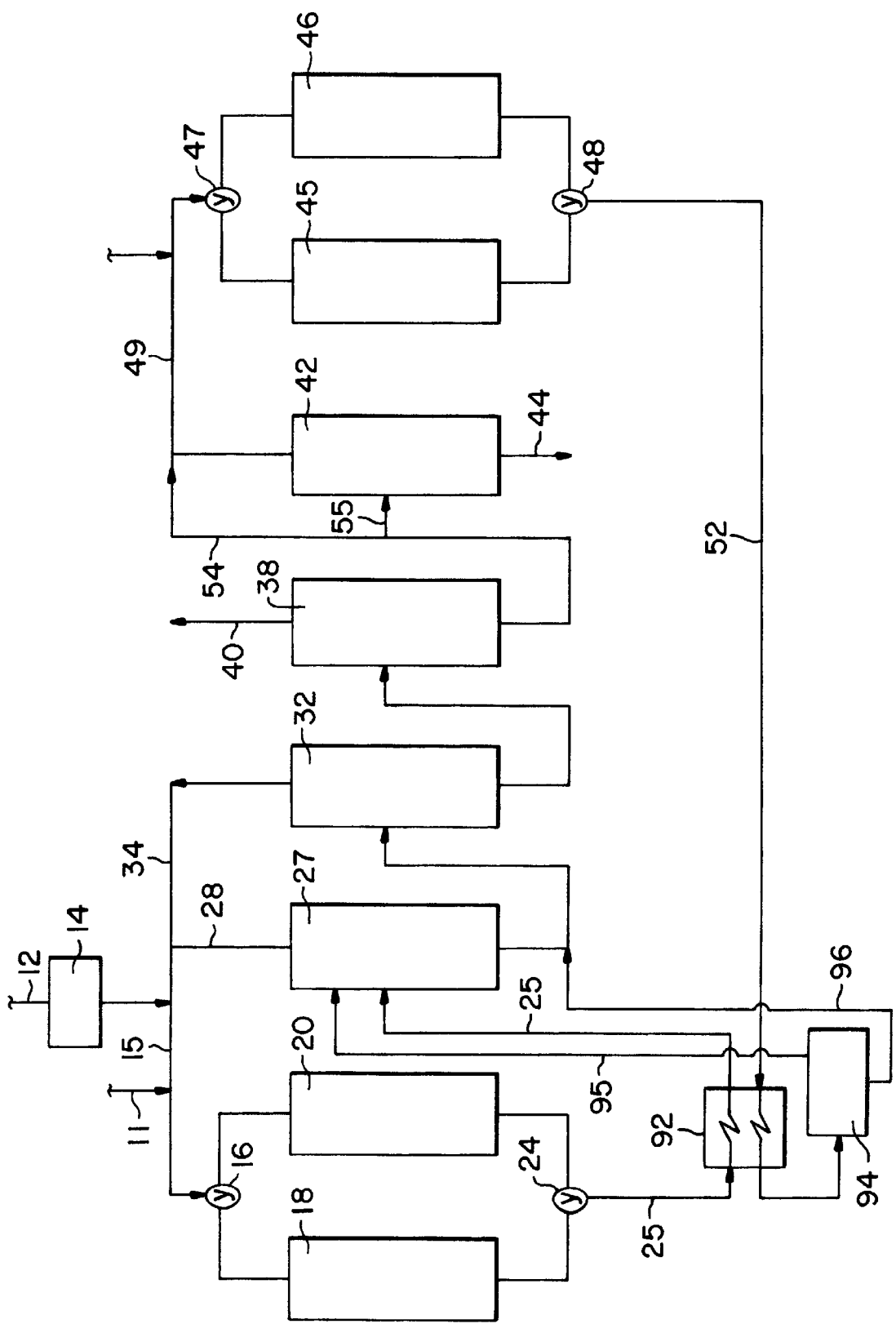
FIG. 5 is a schematic illustration of yet a further modification employing yet another arrangement of heat exchangers together with the use of a flash vessel interposed in the relation of the transalkylation reaction zone.

FIG. 5 illustrates yet another embodiment of the invention in which the transalkylation reactor output is passed in a heat exchange relationship with all or part of the effluent from the alkylation reactor and then passed through a separation zone where the transalkylation reactor output is separated into two fractions. The lighter, lower boiling, fraction is applied to the benzene separation zone, specifically to an upper tray of the benzene prefractionation column 27. The heavier, higher boiling, fraction is applied to the feed stream to the benzene recovery column 32.

FIG. 5 illustrates this embodiment as a modification of the process scheme of FIG. 3 modified as described previously to split the transalkylation reactor output into two fractions. In FIG. 5, like components as are used in FIG. 3 are illustrated by the same reference numerals as shown in FIG. 3. As shown in FIG. 5, the transalkylation reactor effluent is passed through valve 48 to line 52 and thence to a heat exchange zone 92. In heat exchange zone 92, the transalkylation reactor effluent is passed in indirect heat exchange with the alkylation reactor effluent withdrawn via line 25. The transalkylation reactor output from heat exchanger 92 is applied to a separation zone in the form of a flash vessel 94 where the pressure is reduced, e.g. from about 600 psia to about 250 psia to produce a lighter boiling fraction withdrawn via line 95 and a heavier, higher boiling, fraction withdrawn via line 96. The output through line 96 is recombined with the bottoms of the benzene pre-fractionation column and then passed to the initial benzene separation column 32. The lighter boiling fraction of the transalkylation reactor effluent is withdrawn from separator 94 through line 95 and applied to an earlier stage of the benzene recovery column 32, e.g. an upper tray in the case of a tray-type fractionation column or an upper portion of the packing in a packing type fractionation vessel. The heat exchange zone 92 may take the form of a multi-stage heat exchange configuration as described above with reference to FIG. 4 or be of any other suitable configuration.

As noted previously in the preferred embodiment of the invention, at least a portion of the output from the transalkylation reactor is applied to the first stage of the benzene recovery zone, column 27. This is in contrast to the conventional procedure where multistage benzene separation is practiced of supplying the recycling transalkylation output to the second stage. In yet a further embodiment of the invention, employing a multistage benzene separation zone, the transalkylation reactor output is passed in a heat exchange relationship with a portion of the effluent from the alkylation reactor and then passed to a separation zone in accordance with the embodiment of FIG. 5. However, where the overhead fraction may be applied directly to the initial benzene separation column 27 as shown in FIG. 5, the second heavier bottoms fraction withdrawn via line 96 may be supplied to the secondary stage of the benzene separation zone (column 32). In this embodiment, the fraction in line 36, rather than being combined with line 25, as shown in FIG. 5, is instead applied directly to column 32.

Having described specific embodiments of the present invention, it will be understood that modifications thereof may be suggested to those skilled in the art, and it is intended to cover all such modifications as fall within the scope of the appended claims.

What is claimed:

1. In an alkylation-transalkylation process, the steps comprising:
   a) supplying a feedstock containing benzene into a multistage alkylation reaction zone comprising having a plurality of series connected catalyst beds each containing a pentasil molecular sieve aromatic alkylation catalyst comprising predominantly monoclinic silicalite having an average crystal size of about 0.5 micron or less and formulated with an alumina binder to provide catalyst particles having a surface area/volume ratio of at least 60 in$^{-1}$;
   b) supplying a $C_2$–$C_4$ alkylating agent to said reaction zone;
   c) operating said reaction zone at temperature and pressure conditions to maintain said feedstock in the gaseous phase and causing gas-phase alkylation of said benzene by said alkylating agent in the presence of said catalyst to produce an alkylated product comprising a mixture of monoalkylated and polyalkylated aromatic components;
   d) recovering said alkylated product from said reaction zone and supplying said product from said reaction zone to a benzene recovery zone for the separation of benzene substrate from alkylation product;
   e) operating said benzene recovery zone to produce a lower boiling benzene containing fraction and a higher boiling fraction comprising a mixture of monoalkylated aromatic and polyalkylated aromatic component;
   f) recycling benzene from said benzene recovery zone to said reaction zone;
   g) supplying said higher boiling fraction from said benzene recovery zone to a secondary separation zone;
   h) operating said secondary separation zone to produce a second lower boiling fraction comprising a monoalkylated aromatic component and a higher boiling fraction comprising a heavier polyalkylated aromatic component including dialkylated and trialkylated aromatic compounds;
   i) separating said polyalkylated aromatic component into first and second portions of said polyalkylated aromatic component and supplying a first portion of said polyalkylated aromatic component including dialkylated and trialkylated aromatics in said polyalkylated product to a transalkylation reaction zone containing a zeolite transalkylation catalyst comprising a molecular sieve having a pore size greater than the pore size of said pentasil catalyst;
   j) supplying a second portion of said polyalkylated aromatic component from said secondary separation zone to a tertiary separation zone which is operated to separate said heavier polyalkylated aromatic component into a lower boiling fraction of said polyalkylated aromatic component comprising dialkyl and trialkylated aromatics and a higher boiling fraction comprising a residue fraction;
   k) supplying said lower boiling fraction of said polyalkylated aromatic component from said tertiary separation zone to said transalkylation reaction zone in addition to said first portion from said secondary separation zone;
   l) supplying benzene to said transalkylation zone;
   m) operating said transalkylation reaction zone under temperature and pressure conditions to maintain said feedstock in the liquid phase and effective to cause disproportionation of said polyalkylated aromatic fraction to arrive at a disproportionation product having a reduced polyalkyl benzene content and an enhanced monoalkyl benzene content; and
   n) supplying at least a portion of said disproportionation product to said benzene recovery zone.

2. The process of claim 1, wherein said alkylating agent is an ethylating or propylating agent.

3. The method of claim 2, wherein said alkylating agent is ethylene or propylene.

4. The method of claim 3, wherein said alkylating agent is ethylene.

5. The method of claim 4, wherein said benzene recovery zone is operated in a first stage in which a portion of benzene is recovered overhead from said alkylated product and a second stage in which additional benzene is recovered overhead from said alkylated product with benzene is recycled from both said first and second stage of said benzene recovery zone to said reaction zone.

6. The method of claim 5, wherein set at least portion of said disproportionation product from said transalkylation reactor is supplied to said first stage of said benzene recovery zone.

7. The method of claim 6, wherein substantially all of said disproportion product from said transalkylation reactor is supplied to said first stage of said benzene recovery zone.

8. In an alkylation-transalkylation process, the steps comprising:
   a) supplying a feedstock containing benzene into a multistage alkylation reaction zone having a plurality of series connected catalyst beds each containing a pentasil molecular sieve aromatic alkylation catalyst comprising predominately monoclinic silicalite having an average crystal size of about 0.5μ or less and formulated with an alumina binder to provide catalyst particles having a surface area/volume ratio of at least 60 in.$^{-1}$ b) supplying a $C_2$–$C_4$ alkylating agent to said reaction zone;

c) operating said reaction zone at temperature and pressure conditions to maintain said feedstock in the gaseous phase and causing gas-phase alkylation of said benzene by said alkylating agent in the presence of said catalyst to produce an alkylated product comprising a mixture of monoalkylated and polyalkylated aromatic components;

d) recovering said alkylated product from said reaction zone and supplying said product from said reaction zone to a benzene recovery zone for the separation of benzene substrate from alkylation product;

e) operating said benzene recovery zone to produce a lower boiling benzene containing fraction and a higher boiling fraction comprising a mixture of monoalkylated aromatic and polyalkylated aromatic component, f) recycling benzene from said benzene recovery zone to said reaction zone;

g) supplying said higher boiling fraction from said benzene recovery zone to a secondary separation zone;

h) operating said secondary separation zone to produce a secondary lower boiling fraction comprising a monoalkylated aromatic component and a higher boiling fraction comprising a heavier polyalkylated aromatic component;

i) supplying at least a portion of said polyalkylated aromatic component including the dialkylated and trialkylated aromatics in said polyalkylated component to a transalkylation reaction zone containing a zeolite y transalkylation catalyst;

j) supplying benzene to said transalkylation zone;

k) operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content and;

l) supplying at least a portion of said disproportionation product to said benzene recovery zone.

9. The process of claim 8, wherein said alkylating agent is an ethylating or propylating agent.

10. The method of claim 9, wherein said alkylating agent is ethylene or propylene.

11. The method of claim 10, wherein said alkylating agent is ethylene.

12. The method of claim 11, wherein at least some of said heavier polyalkylated aromatic component from said secondary separation zone is, prior to step (i), applied to a tertiary separation zone wherein said heavier polyalkylated aromatic component is separated into a tertiary lower boiling fraction of said polyalkylated aromatic component comprising dialkyl and trialkyl aromatics and a heavier higher boiling residue fraction and wherein said tertiary lower boiling fraction of said polyalkylated aromatic component is supplied to said transalkylation reaction zone in accordance with step (k).

13. The method of claim 12, wherein a first portion of the heavier polyalkylated aromatic component is supplied to said tertiary separation zone in accordance with claim 12 and thence from said tertiary separation zone to said transalkylation zone and a second portion of said heavier polyalkylated aromatic component from said secondary separation zone is supplied directly to said transalkylation zone.

14. The method of claim 13, wherein the ratio of said second portion to said first portion of said heavier polyalkylated component from said secondary separation zone is within the range of 3:1 to 1:3.

15. The method of claim 13, wherein the ratio of said second portion to said first portion of said heavier polyalkylated component from said secondary separation zone is within the range of 2:1 to 1:2.

16. The method of claim 13, wherein said benzene recovery zone is operated in a first stage in which a portion of benzene is recovered overhead from said alkylated product and a second stage in which additional benzene is recovered overhead from said alkylation product and benzene is recycled from both said first and second stage of said benzene recovery zone to said benzene reactor.

17. The method of claim 16, wherein set at least portion of said disproportionation product from said transalkylation reactor is supplied to said first stage of said benzene recovery zone.

18. In an alkylation-transalkylation process, the steps comprising:

a) supplying a feedstock containing benzene into a multistage alkylation reaction zone having at least three series connected catalyst beds each containing a silicalite aromatic alkylation catalyst comprising predominantly monoclinic silicalite having an average crystal size of about 0.5 micron or less and formulated with an alumina binder to provide catalyst particles having a surface area/volume ratio of at least 60 in$^{-1}$;

b) supplying a $C_2$–$C_4$ alkylating agent to said reaction zone;

c) operating said reaction zone at temperature and pressure conditions to maintain said feedstock in the gaseous phase and causing gas-phase alkylation of said benzene by said alkylating agent in the presence of said catalyst to produce an alkylated product comprising a mixture of monoalkylated and polyalkylated aromatic components;

d) recovering said alkylated product from said reaction zone and supplying said product from said reaction zone to a benzene recovery zone for the separation of benzene substrate from alkylation product;

e) operating said benzene recovery zone to produce a lower boiling benzene containing fraction and a higher boiling fraction comprising a mixture of monoalkylated aromatic and polyalkylated aromatic component, f) recycling benzene from said benzene recovery zone to said reaction zone;

g) introducing said alkylating agent to said reaction zone in a manner to provide for the injection of an initial portion of said alkylating agent together with benzene to the top of a first of said catalyst beds with the additional interstage injection of a second portion of said alkylating agent between at least some of said catalyst beds;

h) supplying said higher boiling fraction from said benzene recovery zone to a secondary separation zone;

i) operating said secondary separation zone to produce a second lower boiling fraction comprising a monoalkylated aromatic component and a higher boiling fraction comprising a heavier polyalkylated aromatic component;

j) supplying at least a portion of said polyalkylated aromatic component including substantially all of the dialkylated and trialkylated aromatics in said polyalkylated product to a transalkylation reaction zone containing a zeolite y transalkylation catalyst;

k) supplying benzene to said transalkylation zone;

l) operating said transalkylation reaction zone under temperature and pressure conditions to maintain said feedstock in the liquid phase and effective to cause disproportionation of said polyalkylated aromatic fraction to arrive at a disproportionation product having a reduced polyalkyl benzene content and an enhanced monoalkyl benzene content; and m) supplying at least a portion of said disproportionation product to said benzene recovery zone.

19. The method of claim 18, wherein said alkylation reaction zone is operated to provide an average temperature for said reaction zone of no more than 800° F.

20. The method of claim 18, wherein said alkylation reaction zone comprises at least four series connected catalyst beds wherein said $C_2$–$C_4$ alkylating agent is injected interstage between at least some catalyst beds so that the benzene to $C_2$–$C_4$ alkylating agent ratio of benzene and $C_2$–$C_4$ alkylating agent introduced into said reaction zone is progressively decreased from the top to the bottom of said reaction zone.

* * * * *